United States Patent [19]

Arndt et al.

[11] Patent Number: 4,917,987
[45] Date of Patent: Apr. 17, 1990

[54] METHOD OF ENHANCING THE RESOLUTION OF A FINGERPRINT IMAGE IN A FINGERPRINT RECORDING SYSTEM

[75] Inventors: Douglas C. Arndt, Thousand Oaks; Virgle L. Hedgcoth, Pomona, both of Calif.

[73] Assignee: Identicator Corporation, San Bruno, Calif.

[21] Appl. No.: 269,430

[22] Filed: Nov. 9, 1988

[51] Int. Cl.$^4$ .......................... G03C 5/16; A61B 5/10
[52] U.S. Cl. .................................... 430/139; 430/395; 427/1
[58] Field of Search ...................... 427/1; 430/21, 290, 430/291, 292, 139, 395; 106/19, 20

[56] References Cited

U.S. PATENT DOCUMENTS

| | | | |
|---|---|---|---|
| 2,066,535 | 1/1937 | Lucas | 427/1 |
| 4,176,205 | 11/1979 | Molina | 427/1 |
| 4,504,408 | 3/1985 | Morton | 252/301 |
| 4,708,882 | 11/1987 | Asano et al. | 427/1 |

Primary Examiner—Jose Dees
Assistant Examiner—Jackie Weddington
Attorney, Agent, or Firm—Jackson & Jones

[57] ABSTRACT

A method for enhancing fingerprint images comprises the steps of applying a chemical compound to the fingers to be printed in which the compound contains a first constituent in the form of a conventional ink or inkless reagent. The first constituent is arranged by itself (i.e., ink) or in conjunction with a developer (i.e., inkless) to provide a visible image of a fingerprint when applied to a porous surface, such as a conventional fingerprint card under light within the visible spectrum. A second constituent is included in the compound which is arranged to fluoresce within the visible spectrum (i.e., 500 to 650 nm) when subject to U.V. radiation, preferably centered at 550 nm.

The compound from the fingers is then deposited onto a porous surface and a visible image is formed therefrom representing the ridge patterns of the fingers. The surface is then illuminated with visible and ultraviolet light and the fluorescence of the second constituent enhances the brightness of the image. The image is focused onto a photosensitive surface (e.g., video camera tube or photographic film) having a maximum sensitivity to light within the yellowish-green spectrum and the image is converted into information representative of the ridge patterns of the fingers (e.g., by computer or development of the film.

22 Claims, 1 Drawing Sheet

METHOD OF ENHANCING THE RESOLUTION OF A FINGERPRINT IMAGE IN A FINGERPRINT RECORDING SYSTEM

BACKGROUND OF THE INVENTION

1. Field of the Invention

The present invention relates to fingerprint recording systems and more particularly to a method of enhancing the resolution of the recorded fingerprints.

2. Description of the Prior Art

The art of fingerprinting and identifying persons by their fingerprints is well known. Both ink and inkless methods of taking a person's fingerprints are in widespread use. Either a colored ink or a colorless reagent is applied to an individual's fingers and subsequently the fingers are rolled (or pressed) onto a clean recording surface, such as paper, to deposit the ink or reagent on the surface in a pattern corresponding to the individual's fingerprints. In the inkless method, an additional chemical or reagent is applied to the surface to develop the print so that it is visible. See, for example, U.S. Pat. No. 4,262,623 assigned to the assignee of the present application.

Fingerprints are conventionally taken on fingerprint cards which have been standardized by many governmental agencies such as the U.S. Federal Bureau of Investigation. Such cards normally contain the prints of the individual fingers of each hand.

For efficient recordation purposes the cards may be (1) optically read and the information thereon converted to geometric figures or digital data and stored in a computer memory or (2) photographed and stored on microfilm. With either type of recording system there is need for a clear print of high contrast (between the ridge endings and ridge bifurcations (minutiae) of each person's fingerprint. In addition, the fingerprint patterns on the cards may be transmitted via a facsimile machine.

It has been discovered that the conventional optical readers (using silicon detectors), photographic film (for microfilm recorders) and facsimile transmission apparatus have a peak of photopic response or spectral sensitivity at a wavelength of about 550 nanometers (nm) in the visible yellowish-green region. In each case the light source used to illuminate the fingerprint cards generates some ultraviolet light.

SUMMARY OF INVENTION

The resolution of a fingerprint image in a recording and storage system is enhanced in accordance with the present invention by applying a solution of a chemical compound to the fingerprint pattern area of a least one finger of the person to be fingerprinted. The compound contains a first constituent (e.g. conventional ink or inkless reagent) which is arranged by itself (i.e. ink) or in conjunction with a developer compound (i.e. inkless) to provide a visible image of a fingerprint when applied to a porous surface (e.g. paper fingerprint card) under light within the visible spectrum. The compound further contains a second constituent which is arranged to fluoresce within 500 to 650 nm when subjected to ultraviolet radiation.

The solution from the ridges of the fingerprint pattern is then deposited onto a porous surface and a visible image is formed therefrom representative of the ridge pattern of the finger. The porous surface is illuminated with visible and ultraviolet light whereby the brightness of the image within said predetermined spectrum is increased due to the fluorescence of the second constituent.

The image is focused onto a photosensitive surface (e.g. photoconductivity surface of a video camera or of a facsimile machine or photographic film) having a maximum sensitivity to light within said predetermined range and the image is then converted into information representative of the ridge patterns of the finger (e.g. by computerized conversion to geometrical or digital data or by development of photographic film).

The features of the present invention, which is believed to be novel, are set forth with particularly in the appended claims. The present invention both as to the organization and operation, thereof, may be best understood by reference to the following description taken in conjunction with the accompanying drawing.

DESCRIPTION OF THE PREFERRED EMBODIMENT

Figure 1:
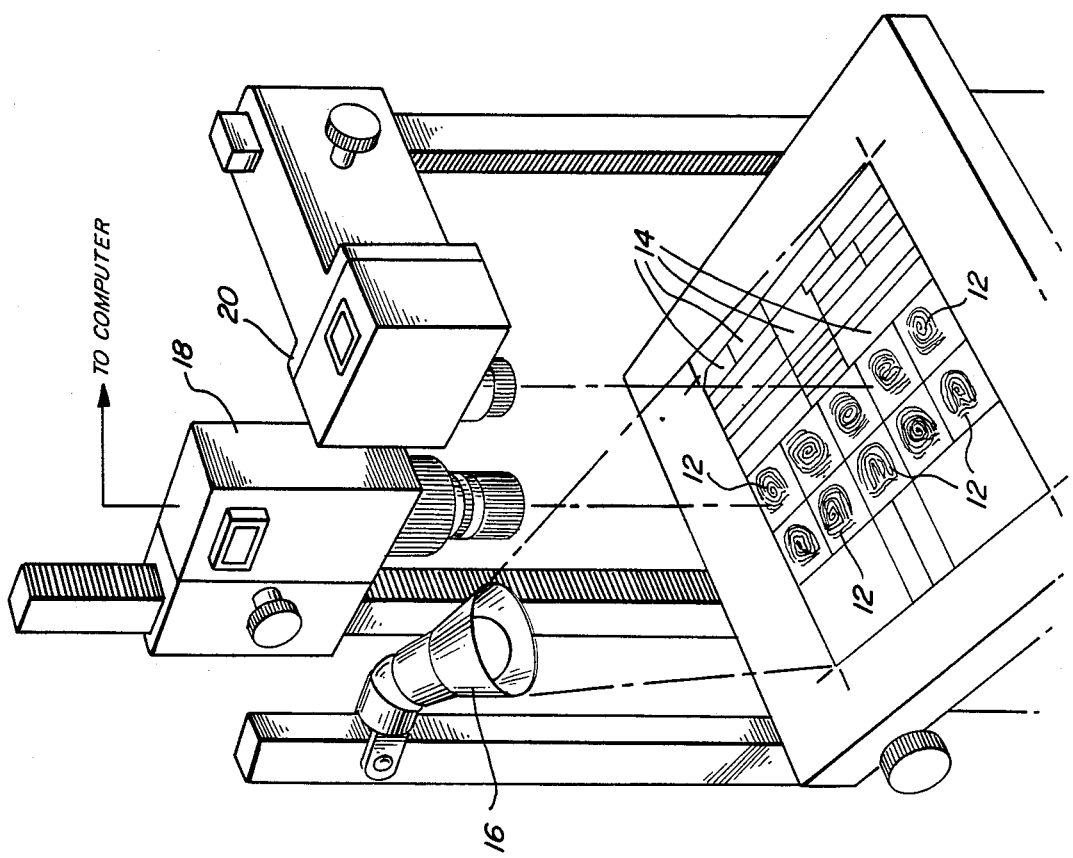
FIG. 1 is a perspective view of a standard fingerprinting card with a video and photographic camera for recording the fingerprint images thereon.

Referring now to FIG. 1 there is illustrated a standard fingerprint card 10 of the type used by many governmental agencies. The card contains ten separate prearranged spaces 12 for receiving the print of the individual fingers of each hand of the person being fingerprinted. The card also contains a group of separate spaces indicated at 14 above the areas on which the identification of the person being fingerprinted is to be typed or printed. The spaces below the areas 12 may be used for additional prints of all four fingers simultaneously.

In accordance with the present invention a solution of a chemical fingerprinting compound containing a first and second constituent is first prepared. The first constituent may comprise either a (1) conventional fingerprinting ink such as carbon black particles suspended in a suitable carrier solution (e.g., mineral oil, alcohol or glycol) or (2) an inkless reagent such as that described in the U.S. Patent 4,029,012 ("'012 patent"). The second constituent comprises a fluorescent material which is arranged to fluoresce within the wavelength range of 500 to 650 nm and preferably centered at about 550 nm (yellowish-green) when subjected to ultraviolet radiation.

The chemical compound solution is then applied to the fingers of the person to be fingerprinted. The fingers of the person are then pressed or rolled onto a porus surface such as the areas 12 on the fingerprint card 10 to deposit the solution from the ridges of the finger thereon.

If an inkless reagent is used in the fingerprinting solution then a developer such as that described in the '012 patent is applied to the latent fingerprint images on the card 10 to render the images visible under ordinary light.

To complete the recordation and storage of the prints, the porous surface of card 10 is then illuminated with a light source 16 which emits light within the visible and ultraviolet spectrum. The information on the card 10 is then either read by a conventional video camera 18 or microfilm camera 20, each having an optimum photopic response (i.e., spectral sensitivity) in the visible spectrum between about 500 to 650 nm and a peak response at about 550 nm.

Figure 2:
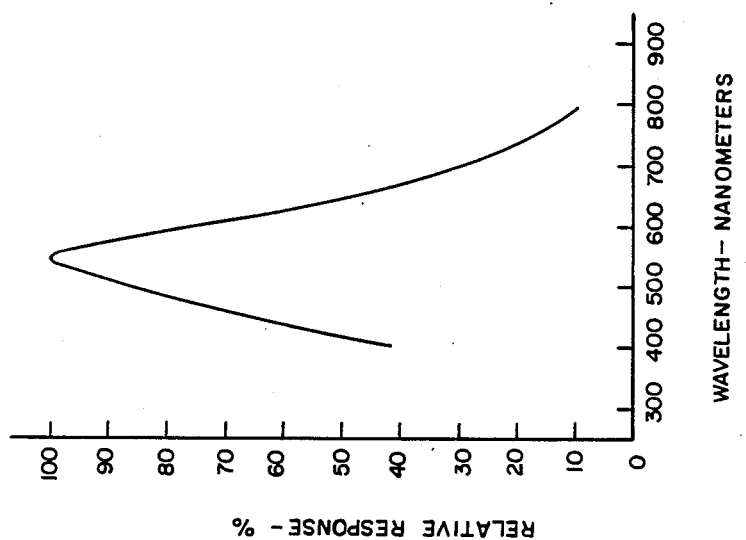
FIG. 2 is a graph showing the spectral response of a video camera commonly used to read fingerprints and record information therefrom.

The spectral sensitivity of an RCA Vidicon tube Model No. 8541 or 8541A which is widely used for recording fingerprints is illustrated in FIG. 2.

In addition to the recordation of fingerprints by video or microfilm camera, the prints on a fingerprint card may be recorded by a local facsimile machine (not shown) and the information thereon transmitted to a remote facsimile machine and printed out as is well known in the art. A facsimile machine specifically designed for this purpose is distributed by Litton System, Inc., Amecom Division, under the model name Policefax (a Litton registered trademark). Such machines have a spectral sensitivity and light source similar to that described above, that is, a peak spectral sensitivity within the range of about 500 to 650 nm and a light source which emits light within the visible as well as the U V. spectrum.

The first constituent of the chemical compound may comprise either a conventional ink or an inkless regent as discussed above. A conventional ink may comprise a suitable solution (in glycol, alcohol or mineral oil) of one or more of the fingerprint powders described in U.S. Pat. No. 4,226,740.

An inkless reagent, as is pointed out in the '012 patent, may comprise as the active ingredient 8-hydroxyquinoline derivatives where X and Y can be any of the following group on the basic structure:

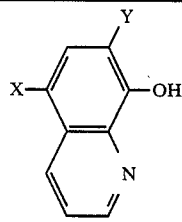

| X | Y |
|---|---|
| H | H |
| SO$_3$H | SO$_3$H |
| SO$_3$H | H |
| H | SO$_3$H |
| SO$_3$H | I |
| SO$_3$H | Br |
| SO$_3$H | Cl |
| Br | Br |
| Br | SO$_3$H |
| Cl | Cl |
| I | I |
| SO$_3$H | NO$_2$ |
| NO$_2$ | SO$_3$H |

Preferably the reagent is propyl gallate or a salt of 8-quinolinol, dimethyldithiocarbamic acid sodium salt dihydrate, sodium ferrocyanide, sodium nitrate, potassium thiocyanate or 8-hydroxyquinoline sulfate. The above regents chemically llreact with a suitable liquid developer solution containing a metallic salt such as ferric chloride to produce a change in color of the medium or ink absorbent coating e.g. black on a white background. Other examples of salts of metals and transition metals for use in the developer solution may be found in the '012 patent.

The second constituent (i.e., fluorescent material) comprises about 0.5% to 20% weight/volume ("w/v") of the total chemical compound solution. Where a fluorescent dye is used as the fluorescent material the percentage will be in the lower end of the range e.g. 0.5% to 5% w/v. I have found that a fluorescent dye called Acridine Yellow G provides an increased minutia count in fingerprint recording systems when added to a conventional fingerprint ink or an inkless regent as described above.

The Acridine Yellow G fluorescent dye comprised about 0.5 to 1% w/v of the total fingerprint compound solution applied to the fingers.

The use of the fluorescent additive not only enhances the resolution of otherwise readable print but makes light prints with little contrast readable by video, microfilm or fax cameras where such prints within the fluorescent additive would either register very poorly or not at all.

There has thus been described a method for enhancing the resolution of recorded fingerprints. Various modifications will be apparent to those skilled in the art without involving any departure from the spirit and scope of my invention as defined in the appended claims.

What is claimed is:

1. A method of enhancing the resolution of a fingerprint image in a fingerprint recording system comprising:
   (a) applying a solution of a chemical fingerprint compound to the fingerprint pattern area of a least one finger of the person to be fingerprinted, the compound containing a first constituent which is arranged by itself or in conjunction with a developer compound to provide a visible image of the fingerprint when applied to a porous surface under light within the visible spectrum and a second constituent which is arranged to fluoresce within a predetermined wavelength range of 500 to 650 nm when subjected to ultraviolet radiation.
   (b) depositing the solution from the ridges of the fingerprint pattern area onto a porous surface and forming a visible image therefrom representative of the ridge pattern of the finger,
   (c) illuminating the porous surface with the fingerprint image deposited thereon with visible and ultraviolet light whereby the brightness of the image within said predetermined spectrum is increased due to the fluorescence of the second constituent.
   (d) focusing the image onto a photosensitive surface having a maximum sensitivity to light within said predetermined range and
   (e) converting the image focused onto the photosensitive surface into information representative of the ridge pattern of the finger.

2. The method of claim 1 wherein the amount of material arranged to fluoresce (fluorescent material) in the chemical fingerprint compound solution, is within the range of about 0.5 to 20% w/v.

3. The method of claim 2 wherein the fluorescent material is a dye.

4. The method of claim 3 wherein the dye is Acridine Yellow G.

5. The method of claim 4 wherein the amount of dye is within the range of about 0.5 to 1% w/v.

6. The method of claim 2 wherein the first constituent is a substantially colorless reagent which when combined with said developer compound provides a visible image.

7. The method of claim 6 wherein the first constituent includes one of the salts of 8-quinolinol, dimethyldithiocarbamic acid sodium salt dihydate, sodium ferrocyanide, sodium nitrate, potassium thiocyanate or 8-hydroxyquinoline sulfate and propyl gallate.

8. The method of claim 7 wherein the developer is ferric chloride.

9. The method of claim 3 wherein the first constituent includes a solvent and carbon black.

10. A method of enhancing the resolution of a fingerprint image in a fingerprint recording system comprising
(a) applying a solution of a chemical fingerprint compound to the fingerprint pattern area of at least one finger of the person to be fingerprinted, the compound containing a first constituent which is arranged to provide a visible image of the fingerprint when applied to a porous surface under light within the visible spectrum and a second constituent which is arranged to fluoresce within a predetermined wavelength range of 500 to 650 nm when subjected to ultraviolet radiation.
(b) depositing the solution from the ridges of the fingerprint pattern area onto a porous surface and forming a visible image therefrom representative of the ridge pattern of the finger.
(c) illuminating the porous surface with the fingerprint image deposited thereon with visible and ultraviolet light whereby the brightness of the image within said predetermined spectrum is increased due to the fluorescence of the second constituent.
(d) focusing the image onto a photosensitive surface having a maximum sensitivity to light within said predetermined range and
(e) converting the image focused onto the photosensitive surface into information representative of the ridge pattern of the finger.

11. The method of claim 10 wherein the amount of arranged to fluoresce (fluorescent material) in the chemical fingerprint compound is within the range of about 0.5 to 20% w/v.

12. The method of claim 13 wherein the fluorescent material is a dye.

13. The method of claim 12 wherein the dye is Acridine Yellow G.

14. The method of claim 13 wherein the amount of the dye is within the range of about 0.5 to 1% w/v.

15. The method of claim 14 wherein the first constituent includes a solvent and carbon black.

16. A method of enhancing the resolution of fingerprint image in a fingerprint recording system comprising:
(a) applying a solution of a chemical fingerprint compound to the fingerprint pattern area of a least one finger of the person to be fingerprinted, the compound containing a first constituent which is arranged in conjunction with a developer compound to provide a visible image of the fingerprint when applied to a porous surface under light within the visible spectrum and a second constituent which is arranged to fluorescence within a predetermined wavelength range of 500 to 650 nm when subjected to ultraviolet radiation.
(b) depositing the solution from the ridges of the fingerprint pattern area onto a porous surface,
(c) applying the developer to area of the porous surface which received the solution to form a visible image representative of the ridge pattern of the finger,
(d) illuminating the porous surface with the fingerprint image deposited thereon with visible and ultraviolet light whereby the brightness of the image within said predetermined spectrum is increased due to the fluorescence of the second constituent.
(e) focusing the image onto a photosensitive surface having a maximum sensitivity to light within said predetermined range and
(f) converting the image focused onto the photosensitive surface into information representative of the ridge pattern of the finger.

17. The method of claim 16 wherein the amount of arranged to fluoresce (fluorescent material) material in the chemical fingerprint compound is within the range of about 0.5 to 20% w/v.

18. The method of claim 17 wherein the fluorescent material is a dye.

19. The method of claim 18 wherein the dye is Acridine Yellow G.

20. The method of claim 17 wherein the first constituent is a substantially colorless reagent which when combined with said developer compound provides a visible image.

21. The method of claim 20 wherein the first constituent includes one of the salts of 8-quinolinol, dimethyldithiocarbamic acid sodium salt dihydate, sodium ferrocyanide, sodium nitrate, potassium thiocyanate or 8-hydroxyquinoline sulfate and propyl gallate.

22. The method of claim 21 wherein the developer compound is a solution of ferric chloride.

* * * * *

UNITED STATES PATENT AND TRADEMARK OFFICE
CERTIFICATE OF CORRECTION

PATENT NO. : 4,917,987

DATED : April 17, 1990

INVENTOR(S) : Douglas C. Arndt and Virgle L. Hedgcoth

It is certified that error appears in the above-identified patent and that said Letters Patent is hereby corrected as shown below:

Column 3, line 21, "U V." should read --U.V.--.

Column 3, line 59, "llreact" should read --react--.

Column 5, line 8, "3" should read --2--.

Column 5, line 42, before "arranged" should be --material--.

Column 5, line 45, "13" should read --11--.

Column 6, line 34, before "arranged" should be --material--.

Column 6, line 34, after "(fluorescent material)" delete "material".

Signed and Sealed this

Twenty-eighth Day of May, 1991

Attest:

HARRY F. MANBECK, JR.

Attesting Officer

Commissioner of Patents and Trademarks